United States Patent
Bisgaard (10) Patent No.: US 8,165,329 B2
(45) Date of Patent: Apr. 24, 2012

(54) HEARING INSTRUMENT WITH USER INTERFACE

(75) Inventor: Nikolai Bisgaard, Kgs. Lyngby (DK)

(73) Assignee: GN ReSound A/S, Ballerup (DK)

( * ) Notice: Subject to any disclaimer, the term of this patent is extended or adjusted under 35 U.S.C. 154(b) by 365 days.

(21) Appl. No.: 12/521,117

(22) PCT Filed: Dec. 18, 2007

(86) PCT No.: PCT/DK2007/000549
§ 371 (c)(1),
(2), (4) Date: Jun. 24, 2009

(87) PCT Pub. No.: WO2008/074323
PCT Pub. Date: Jun. 26, 2008

(65) Prior Publication Data
US 2010/0067722 A1    Mar. 18, 2010

Related U.S. Application Data

(60) Provisional application No. 60/876,697, filed on Dec. 23, 2006.

(30) Foreign Application Priority Data

Dec. 21, 2006  (DK) .................................. 2006 01690

(51) Int. Cl.
*H04R 25/00* (2006.01)
(52) U.S. Cl. ........................................ 381/314; 381/312
(58) Field of Classification Search ................. 381/23.1, 381/312, 313, 314, 317, 318
See application file for complete search history.

(56) References Cited

U.S. PATENT DOCUMENTS

| 4,425,481 | A |  | 1/1984 | Mansgold et al. |
|---|---|---|---|---|
| 5,636,285 | A |  | 6/1997 | Sauer |
| 2004/0013280 | A1 | * | 1/2004 | Niederdrank ................. 381/315 |
| 2005/0078842 | A1 | * | 4/2005 | Vonlanthen et al. .......... 381/312 |
| 2007/0172088 | A1 | * | 7/2007 | Olsen et al. .................... 381/312 |
| 2007/0269064 | A1 | * | 11/2007 | Allegro-Baumann et al. ............. 381/313 |

FOREIGN PATENT DOCUMENTS

| EP | 0 823 829 A | 2/1998 |
|---|---|---|
| WO | 00 41440 A | 7/2000 |
| WO | 2005 084074 A | 9/2005 |

OTHER PUBLICATIONS

Written Opinion of the International Searching Authority for International Application No. PCT/DK2007/000549. International Preliminary Report on Patentability for International Application No. PCT/DK2007/000549.
International Search Report for International Application No. PCT/DK2007/000549.

* cited by examiner

*Primary Examiner* — Tuan Nguyen
(74) *Attorney, Agent, or Firm* — Vista IP Law Group, LLP (57) ABSTRACT

A hearing instrument includes a microphone for converting sound into an electric audio signal, a signal processor unit coupled to the microphone, the signal processor unit configured for operating in a plurality of states that include at least a first state and a second state, wherein the signal processor unit is configured for automatically switching at least between the first state and the second state according to a switching strategy, a speaker coupled to the signal processor unit, and a user interface that is configured to receive a user feedback regarding an automatic switching between the first state and the second state, wherein the user interface is communicatively connected to the signal processor unit and is configured to provide at least one control signal to the signal processor unit in response to the user feedback, wherein the signal processor unit is configured to receive the control signal in a predetermined input period upon the automatic switching between the first state and the second state.

29 Claims, 6 Drawing Sheets

HEARING INSTRUMENT WITH USER INTERFACE

RELATED APPLICATION DATA

This application is the national stage of International Application No. PCT/DK2007/000549 filed on Dec. 18, 2007, which claims priority to and the benefit of Danish Patent Application No. PA 2006 01690 filed on Dec. 21, 2006, and U.S. Provisional Patent Application No. 60/876,697, filed on Dec. 23, 2006, the entire disclosures of all of which are expressly incorporated by reference herein.

FIELD

The present application relates to a hearing instrument, such as a hearing aid, or an implantable hearing prosthesis, with a user interface for enabling a user to provide feedback to the hearing instrument.

BACKGROUND

Some of the existing hearing aids have multiple modes of operation. The different modes of operation enable the hearing aid to meet as good as possible various general and/or specific needs of the user in different situations or environments. As an example, directionality makes it possible for a hearing aid to "focus" on a sound source, such as a speaking person, located e.g. in front of the wearer of the hearing aid. Thereby, possibly disturbing sounds coming from the sides and back of the wearer will have a limited influence on the wearer's perception of sound from a source in front of him/her. One or more modes of operation may therefore include such beam-forming signal processing.

As another example, a specific acoustical environment may require the use of specific noise suppression and/or other specific signal processing which can therefore be selected as a program or mode of operation. Further, in one or more modes of operation, the hearing aid may make use of a telecoil for receiving audio information from an electromagnetic field.

Since it is quite inconvenient for a hearing impaired person to manually switch between different modes of operation in dependence of his/her needs, several attempts have been made to develop efficient methods for automatically selecting "the best" mode of operation as the listening environment or conditions changes.

Modern hearing aids feature signal processing which is automatically adjusted either in accordance with pre-programmed settings or by continuous, incremental adjustments that are believed to improve the speech intelligibility or listening comfort in the given environment. Often so-called "soft-switching" between modes or states is used in order not to create a sudden and disturbing change in sound quality.

Also, many hearing aids offer the opportunity to force the aid into a certain mode based on the choice of the user. A signal is added into the amplified audio signal to confirm the change of mode. The signal is normally a series of beeps or the like. It has previously been suggested that such signal could be recordings of voice messages.

One of the pitfalls of automatic switching of modes is that the system switches into a mode or state that is not seen as an improvement by the user. It is not given that all users have the same demands in situations that appear similar to the recognition system and it may not be possible to discover that during the fitting process.

SUMMARY

Accordingly it is one objective to provide a hearing instrument enabling a user to evaluate or give feedback on automatic switching between modes or states.

It is also an objective to provide a simple user interface from the user point of view allowing a user to influence the switching strategy of the hearing instrument.

Further, it is an objective to improve user-friendliness of hearing instruments. Furthermore, it is an objective to improve the switching strategy of a hearing instrument configured for automatic switching between states.

According to a first aspect, a hearing instrument is provided, comprising a microphone for converting an audio signal into an input signal, a signal processor unit that is configured for operating in a plurality of states including a first state and a second state, and wherein the signal processor unit is configured for automatic switching between at least the first state and the second state according to a switching strategy, a loudspeaker for conversion of an electrical signal into sound, and a user interface that is connected to the signal processor unit and configured to generate at least one control signal to the signal processor unit in response to a user input, wherein the at least one control signal enables a user of the hearing instrument to provide user feedback. The hearing instrument may be configured to receive user input in a predetermined input period upon the automatic switching between the first state and the second state.

According to a further aspect a method of operating a hearing instrument is provided, the hearing instrument operating according to one or more hearing aid parameters and having a user interface and being configured for automatic switching between a first state and a second state, comprising the steps of:
  monitoring one or more hearing aid parameters in order to identify a state change,
  determining the user feedback settings if a state change has occurred, and
  enable user feedback via the user interface according to the user feedback settings.

The step of enabling user feedback may comprise the step of enabling user feedback in a predetermined input period.

The hearing instrument according to some embodiments described herein may thus allow a user to provide user feedback on the automatic switching between the first state and the second state.

The user interface may be disabled outside the input period and/or the signal processor unit may be configured to ignore user input outside the input period.

The hearing instrument may be configured to operate according to user feedback settings.

It is an advantage of some of the embodiments described herein that a user can evaluate or give feedback on automatic switching between states thereby avoiding undesired operation of the hearing instrument.

Preferably the hearing instrument is configured to operate according to the at least one control signal from the user interface.

The hearing instrument may be any hearing instrument, such as a hearing aid, e.g. behind-the-ear (BTE), in-the-ear (ITE), in-the-canal (ITC), or an implantable hearing prosthesis.

Preferably, the signal processor unit comprises an analysis unit. The analysis unit may be configured to analyze the surroundings with respect to conditions having influence on optimum operation of the hearing instrument, e.g. signal class, such as noise or voice or a combination, noise level, noise type, the presence of an electromagnetic signal detected by a telecoil of the hearing instrument, or a change in physical surroundings, etc. For example, the analysis unit may recognize or identify one or more different environments in which the hearing instrument operates and/or different classes of signals, such as noise or voice. One or more parameters of the signal processing in the signal processor unit may be adjusted automatically according to an output from the analysis unit. The output from the analysis unit may e.g. reflect the environment in which the hearing instrument operates. Changes in the output of the analysis unit and/or adjustment of one or more parameters of the signal processing, e.g. in response to the output from the analysis unit, may be regarded as switching from a first state to a second state.

The signal processor unit may comprise a feedback cancellation unit, e.g. an adaptive feedback cancellation unit, and/or a single or multi-band audio compression unit comprising a filter bank.

The signal processor unit may be configured to receive one or more control signals from the user interface, and may be configured to operate according to the one or more control signals, e.g. switch state upon receipt of a control signal from the user interface. In an embodiment, the signal processor unit is configured to receive a first control signal from the user interface indicating negative feedback, i.e. user dissatisfaction, on the automatic switching from the first state to the second state. The hearing instrument may be configured to switch back to the first state after receipt of the first control signal from the user interface. In an embodiment, the signal processor unit is configured to receive a second control signal from the user interface indicating positive feedback on the automatic switching from the first state to the second state.

The hearing instrument may be configured to receive input from the user, for example continuously or during one or more input periods, e.g. the signal processor unit may be configured to receive at least one control signal from the user interface in a first input period after switching from the first state to the second state. In an embodiment, the hearing instrument is configured to receive user input via the user interface only for certain input periods, e.g. only in a first input period after switching from the first state to the second state. The predetermined input period may be limited in time, and the properties of the predetermined input period may be determined by the user feedback settings.

Enabling a user to provide feedback in a predetermined input period upon automatic switching ensures user evaluation of the correct shift between states. Hereby is achieved that the user feedback is provided within a time period wherein it is highly likely that the user will remember the first state, and thus ensuring a reliable user specific evaluation of the shift between the states.

Further, it is an important advantage of some of the embodiments described herein that a user may be able to provide feedback during normal use of the hearing aid, and thus the time period for providing user feedback is not limited to a training period of a certain length.

The user may also issue multiple control signals within a predefined input period to signal a stronger or weaker preference.

The hearing instrument may be configured for performing so-called soft switching when switching between modes or states. Hereby, when switching from a first mode to a second mode, one or more hearing instrument parameter values are gradually, over time, changed from having a first set of values to a second set of values corresponding to the first mode and the second mode, respectively. In order to enable the user to provide feedback on the automatic switching, the soft switching may be optimized for, on the one hand, avoiding a sudden and disturbing switching and for, on the other hand, enabling the user to perceive and hereby being able to evaluate the benefit of the performed switching. Such an optimization of the soft switching may be achieved by selecting the soft switching period, i.e. the time period in which the parameter values are gradually changed from the first set of parameter values to the second set of parameter values, to have a given preferred duration, e.g. between 0.5 seconds to 10 seconds, and preferably between 1 second and 5 seconds, such as 3 seconds. The length of the soft switching period may advantageously be selected dependent on the type of modes between which the switching is performed.

When performing soft switching, the hearing instrument may be configured to enable positive or negative feedback as described above. When the hearing instrument is configured for enabling the user to provide positive feedback, i.e. enabling the user to accept a proposed shift from a first mode or state to a second mode or state, the hearing instrument may further be configured for ending gradual shifting of operating parameter values during the soft switching when receiving a positive feedback from the user. Further, the hearing instrument may use the intermediate set of operating parameter values, i.e. those operating parameter values achieved during the soft switching at the time when the positive feedback was received, as operating parameter values of the accepted mode of operation. Hereby, the hearing instrument enables the user to accept an intermediate mode of operation, i.e. a state achieved during the transition between the first parameter value set and the second parameter value set, as the mode to be used. The hearing instrument may then continue the operation in this mode.

The operating parameter values corresponding to the user selected intermediate mode may advantageously be stored in the hearing instrument as it provides valuable information about user preferences. Corresponding information relating to the sound environment may also be stored in the hearing instrument. In order to enable the user to select an intermediate mode of operation during soft switching, the soft switching period may advantageously be selected as a trade-off between performing a relatively rapid switching focusing on optimizing the users ability to perceive the switching being performed, and a less rapid switching focusing on enabling the user to select a preferred intermediate mode. The soft switching time may for example be between 0.5 seconds and 10 seconds. As also mentioned above, further user focus on the switching may also be obtained by providing the user with a switching indication signal.

The hearing instrument may be configured for automatic switching between and operation in a plurality of states comprising one or more main states, each main state having one or more sub states. In this case, the automatic switching may be performed according to a switching strategy.

The one or more main states may comprise any suitable number of main states, such as two, three, four, five, six, seven, or more main states, and each main state may comprise any suitable number of sub states, such as one, two, three, four, five, six, seven, or more sub states. In an embodiment, the one or more main states comprise an update state. In the update state, the switching strategy of the hearing instrument may be updated. A main state may be defined by the value of one or more main state parameters, and sub states may in addition to main state parameters be defined by the value of one or more sub state parameters.

The one or more main state parameters may comprise one or more operating parameters, such as one or more preset operating parameters, filter coefficients, delay constants, gain parameters, environment parameters, etc.

The one or more sub state parameters may comprise one or more operating parameters, such as one or more preset operating parameters, filter coefficients, delay constants, gain parameters, environment parameters, etc.

In an embodiment, the first state and the second state are main states. The first state and the second state may be sub states within a main state.

The hearing instrument may be configured to emit one or more indicator signals according to user feedback settings to indicate different changes in the operation of the hearing instrument, such as switching from one state to another, start and/or end of input period(s), user input received, etc. The one or more indicator signals may comprise one or more sound signals, such as one or more beeps, voice message, etc., that are emitted via the loudspeaker. In an embodiment, the one or more indicator signals comprise one or more tactile signals, e.g. a vibration signal.

The hearing instrument may be configured to emit a first indicator signal. The first indicator signal may indicate that the hearing instrument switches from the first state to the second state and/or indicate the beginning of a user input period. The first indicator signal may be a sound signal that is emitted via the loudspeaker and may indicate to the user that a state change will take, takes or has taken place. The first indicator signal may comprise one or more sound beeps, a voice message, etc. The first indicator signal may be emitted before, simultaneously or after the switching from the first state to the second state.

The hearing instrument may be configured to emit a second indicator signal. The second indicator signal may indicate the end of an evaluation period, where a user evaluates the change of state. The second indicator signal may further or alternatively indicate the beginning or the end of a user input period. The second indicator signal may be a sound signal, such as a sound beep, a voice message, etc., emitted via the loudspeaker.

The hearing instrument may be configured to emit a third indicator signal. The third indicator signal may indicate the end of a user input period and/or indicate that user input is received. The third indicator signal may be a sound signal, such as a sound beep, a voice message, etc., emitted via the loudspeaker.

The first, second, and/or the third indicator signal may be emitted before, at the same time as, and/or after switching from the first state to the second state.

The hearing instrument may be configured to perform a compare function that monitors and compares one or more hearing instrument parameters, e.g. state parameters. A certain change in one or more hearing instrument parameters may be regarded as a change from a first state to a second state.

The compare function provides an output, and user feedback settings may be adjusted according to the output of the compare function. The user feedback settings may comprise settings such as input period length, type of indicator signal, indicator signal scheme, etc.

The hearing instrument may be configured to compare the first state and the second state. For example, the hearing instrument may be configured to compare one or more hearing instrument parameters of the first state with one or more hearing instrument parameters of the second state, and the hearing instrument may adjust user feedback settings based on the result of the comparison, for example whether user feedback on the state change is allowed, e.g. in a first input period, and/or if one or more indicator signals are to be emitted to indicate different changes in the operation of the hearing instrument.

Comparison of the first state and the second state may be performed by a compare function $f_{compare}$, e.g. in the signal processor unit or in a compare unit, and the output $X_{compare}$ from the compare function may determine or correspond to the user feedback settings of the hearing instrument. For example, the compare function may determine if the user is allowed to provide feedback on a change state. The compare function may be a static preset function of the hearing instrument, or the compare function may be an adaptive function and may be adjusted during update or continuously during operation of the hearing instrument. The output of the compare function may be expressed as:

$$X_{compare} = f_{compare}(X_{k-M}, \ldots, X_{k-1}, X_k, X_{k+1}, \ldots, X_{k+N}),$$

where the output $X_{compare}$ is a scalar or a vector, and the inputs $X_{k-M}, \ldots, X_{k-1}, X_k, X_{k+1}, \ldots, X_N$ are vectors or scalars. Preferably, $X_{k-M}, \ldots, X_{k-1}, X_k, X_{k+1}, \ldots, X_N$ comprise values of one or more operating parameters to be compared in $f_{compare}$ at times $k-M, \ldots, k-1, k, k+1, \ldots, k+N$, where M and N are integers, and k is the time of the present state. The input to the compare function may comprise the output of the analysis unit and/or a program value indicating a certain program type. The input to the compare function may be based on polling and/or interrupt. The compare function $f_{compare}$ may be a discrete function and/or a logic function. In an embodiment, the compare function $f_{compare}$ may be a vector function having user feedback settings as output $X_{compare}$.

In an embodiment of the compare function, the output of the compare function may be "0" or "1" corresponding to a first set of user feedback settings: "no indicator signal and no input period" and a second set of user feedback settings: "emit indicator signals and enable input", respectively.

In an embodiment, the input to the compare function may comprise a variable indicating which program the hearing instrument operates according to. A change in the program is identified by the compare function and the user feedback settings may be adjusted accordingly.

The input to the compare function may comprise the switching strategy, and/or the compare function may adopt or reflect the switching strategy. Thus, the input to the compare function may comprise prior, present and/or future values of one or more operating parameters, and user feedback settings may be adjusted according to prior, present and/or future values of one or more operating parameters.

The user feedback function of the hearing instrument may be disabled after an initial training period of e.g. 14 days. The hearing instrument may be configured to automatically disable the user feedback function of the hearing aid. A full memory unit may trigger disabling of user feedback.

The operation of the hearing instrument when switching from a first state to a second state may be determined by user feedback settings, e.g. the hearing instrument may allow and/or enable user feedback according to the user feedback settings. The user feedback settings may determine the timing of one or more indicator signals emitted to indicate different changes in the operation of the hearing instrument, the type and content of emitted indicator signals, which indicator signals are to be emitted, timing and/or duration of input periods, etc.

A change of state from a second state to a third state may trigger the beginning of a new predetermined input period for feedback on the change from the second state to the third state. The change of state from a second state to a third state may be regarded as the end of a user input period for feedback regardless of the user feedback settings.

The user feedback settings may be preset, e.g. in a look-up table in hearing instrument memory, or adjusted during operation of the hearing instrument. Preferably, the user feedback settings are adjusted according to the output of the compare function. A first set of user feedback settings may be employed according to a first output, a second set of user feedback settings may be employed according to a second output, a third set of user feedback settings may be employed according to a third output, etc.

The user interface system may also be configured to act as an alerting function. In cases where the operational mode of the hearing develops very gradually and no indicator signals are emitted, the user may force the hearing aid to analyze the situation and apply a new operational mode by using the user interface. This would then trigger a sequence where an indicator signal is emitted and a feedback period is enabled.

A certain indicator signal, e.g. the first indicator signal, the second indicator signal and/or the third indicator signal, may have different content depending on user feedback settings. For example, a certain indicator signal may be a first voice message according to one set of user feedback settings, and a second voice message or a beep according to another set of user feedback settings.

Preferably, the user interface is configured for receiving input from a user. The input from a user may take any suitable form, such as manual, wireless via a remote control, sound input, e.g. voice commands, etc.

In a preferred embodiment, the user interface is configured for automatic voice recognition and generation of a control signal in response to the automatic voice recognition. In an embodiment, the user interface may form an integrated part of the signal processor, e.g. the signal processor unit may be configured for automatic voice recognition.

A hearing instrument with automatic voice recognition may reduce or remove the need for manual input, leading to a simpler user interface from a user's point of view. This is an advantage when considering the small dimensions of a hearing instrument.

In an embodiment, the user interface is a non-manual user interface.

In a preferred embodiment, the user interface comprises a switch or a push-button, and thus the user interface may be configured to receive manual input from a user. The user interface may comprise a plurality of push-buttons or switches; however a user interface with one push-button only may be preferred due to the desire for a simple user interface.

Further, the user interface may comprise a remote control.

The hearing instrument may comprise a memory unit and the hearing instrument may be configured for storing or recording a variable indicating user input from the user interface in the memory unit. Further, the hearing instrument may be configured for storing data, such as a set of variables including one or more operation parameters, e.g. state variables, filter coefficients, environment parameter, delay coefficients, gain coefficients, etc., in the memory unit. Storing of data may be triggered by input from a user. In an embodiment, storing of data, including user input, in the memory unit is triggered by the output of the compare function.

The hearing instrument may be configured to update or adapt the switching strategy based on data stored or recorded in the memory unit. The switching strategy of the hearing instrument may be updated continuously during normal operation. However, updating of a switching strategy may require considerable computation, and thus the plurality of states may include an update state for updating the switching strategy. The hearing instrument may switch to the update state in response to a control signal from the user interface resulting from a user input. Alternatively or in combination, the hearing instrument may be configured to switch to the update state when placed in a docking station, e.g. for recharging. The docking station may be connected to a computer. In one embodiment, the process of switching off the hearing instrument comprises the step of switching to the update state before turning off the hearing instrument.

The compare function of the hearing instrument may be preset, updated continuously during normal operation and/or when the hearing instrument is in an update state.

In an embodiment, the switching strategy may be temporarily amended upon receipt of user feedback in an input period, e.g. the future switching from one state to another state may be blocked if the user has rejected that or a similar switching. The blocking may be removed at update of the switching strategy or after a certain period of time, e.g. after 10 minutes, 1 hour, 5 hours, 1 day, 3 days or more.

In an embodiment, the compare function of the hearing instrument and/or the user feedback settings are adapted continuously based on user input from the user interface. For example, user feedback settings may be adjusted if a user has confirmed switching.

Update of the switching strategy may be performed by the hearing instrument itself. Alternatively, or in combination, update of the switching strategy may be performed by a computer and/or via the Internet.

In an embodiment, the hearing instrument is configured for switching to a third state in response to a third control signal from the user interface. Thereby a user is enabled to switch to a desired state and thereby overriding the environment recognition.

In some embodiments, all user actions are logged in a memory unit of the hearing instrument with one or more operating parameter values.

In accordance with some embodiments, a hearing instrument includes a microphone for converting sound into an electric audio signal, a signal processor unit coupled to the microphone, the signal processor unit configured for operating in a plurality of states that include at least a first state and a second state, wherein the signal processor unit is configured for automatically switching at least between the first state and the second state according to a switching strategy, a speaker coupled to the signal processor unit, and a user interface that is configured to receive a user feedback regarding an automatic switching between the first state and the second state, wherein the user interface is communicatively connected to the signal processor unit and is configured to provide at least one control signal to the signal processor unit in response to the user feedback, wherein the signal processor unit is configured to receive the control signal in a predetermined input period upon the automatic switching between the first state and the second state.

In accordance with other embodiments, a method of operating a hearing instrument that operates according to one or more hearing aid parameters, the hearing instrument having a user interface and being configured for automatic switching between a first state and a second state, the method includes monitoring the one or more hearing aid parameters to identify a state change, determining a user feedback setting, and when the state change is identified, enabling user feedback via the user interface according to the user feedback setting.

Other and further aspects and features will be evident from reading the following detailed description of the embodiments, which are intended to illustrate, not limit, the invention.

BRIEF DESCRIPTION OF THE DRAWINGS

The above and other features and advantages will become more apparent to those of ordinary skill in the art by describing in detail exemplary embodiments thereof with reference to the attached drawings in which.

DETAILED DESCRIPTION

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

Figure 1:
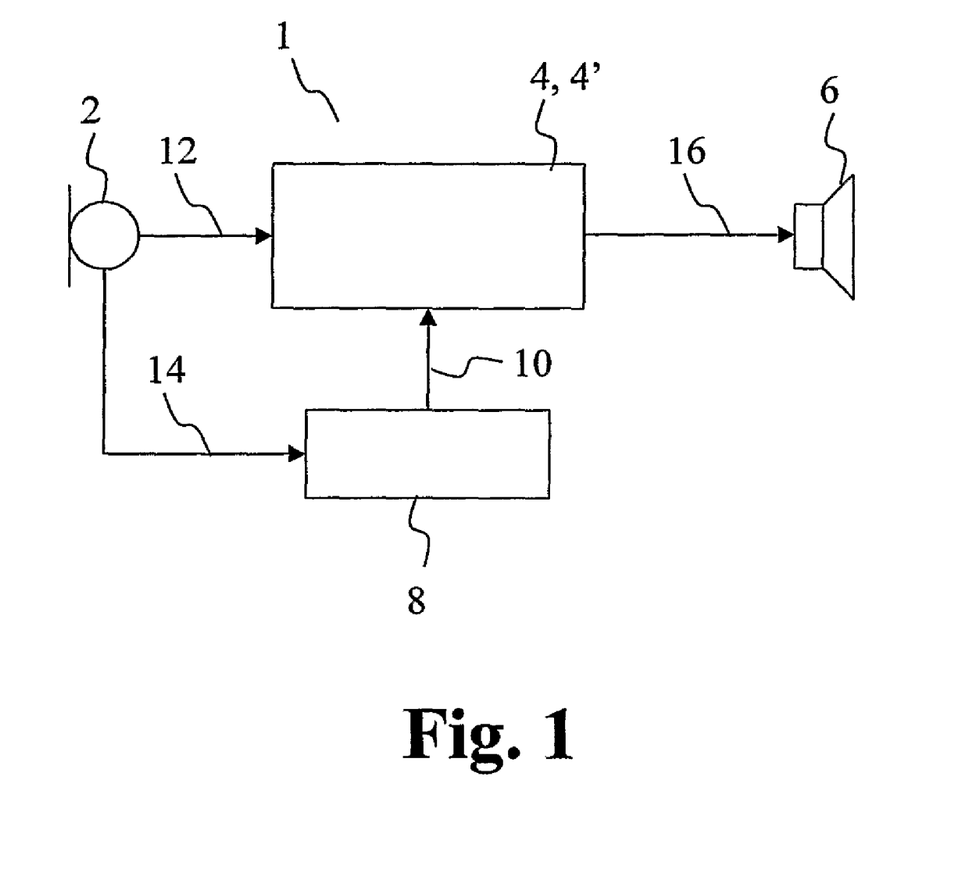
FIG. 1 schematically illustrates an embodiment.

FIG. 1 schematically illustrates an embodiment of a hearing instrument. The hearing instrument comprises a microphone 2 for converting an audio signal into an input signal, a signal processor unit 4 that is configured for operating in a plurality of states including a first state and a second state, and wherein the signal processor unit 4 is configured for automatic switching at least the first state and the second state according to a switching strategy, a speaker 6 (e.g., a loudspeaker) for conversion of an electrical signal into sound, and a user interface 8 that is connected to the signal processor unit 4 via the connection 10 and configured to generate at least one control signal to the signal processor unit 4 in response to a user input, wherein the at least one control signal comprises a first control signal enabling a user of the hearing instrument 1 to provide user feedback on the automatic switching between the first state and the second state.

The input signal 12' is lead to the signal processor unit 4 via connection 12. In an embodiment, the input signal 12' may also be led to the user interface 8 via optional connection 14 for automatic voice recognition enabling the user to provide feedback via the user interface using voice commands.

Figure 2:
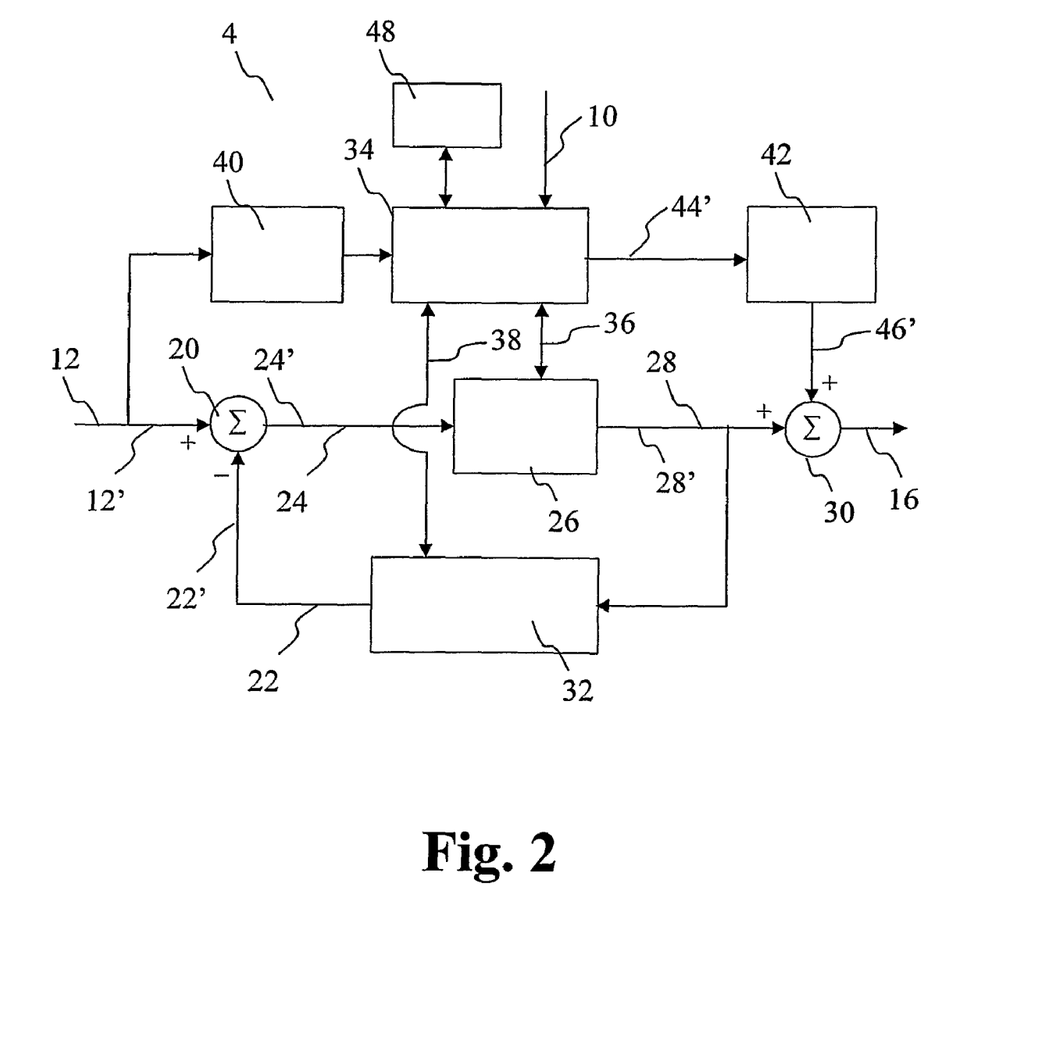
FIG. 2 schematically illustrates an exemplary signal processor unit.

FIG. 2 schematically shows an exemplary signal processor unit 4 for a hearing instrument including acoustic feedback cancellation. The input signal 12' is fed into summation unit 20 with estimated feedback signal 22' on connection 22, the estimated feedback signal 22' compensating undesired acoustic feedback from the loudspeaker to the microphone. The compensated input signal 24' is fed to a processing unit 26 via connection 24. The processing unit 26 may comprise single or multi-band signal processing, and the processed signal 28' is fed to a summer 30 and to feedback cancellation unit 32 via connection 28. The output of the summer is fed to the loudspeaker 6 via connection 16.

The signal processor unit 4 shown in FIG. 2 further comprises a control unit 34. The control unit 34 is connected to the processing unit 26 and the feedback cancellation unit 32 via connections 36, 38, respectively. The control unit 34 may control one or more operating parameters of the signal processing in the processing unit 26 and/or in the feedback cancellation unit 32 depending on output from an analysis unit 40 and/or output from the user interface on connection 10. In one embodiment, the analysis unit 40 is further configured to perform automatic voice recognition.

The control unit 34 may comprise a compare function, thereby being configured to monitor one or more operating parameters of the processing unit 26 and/or the feedback cancellation unit 32. The feedback cancellation unit 32 may be an adaptive feedback cancellation unit, and thus change one or more operating parameters independent of the control unit 34. Operating parameters of the processing unit 26 and/or the feedback cancellation unit 32 may be fed to and/or monitored by the control unit 34 via connections 36 and 38, respectively. Environment recognition may be incorporated in the processing unit 26 and/or in the feedback cancellation unit 32. The signal processor unit 4 in FIG. 2 further comprises a signal generator 42. The signal generator 42 is configured to generate one or more signals in response to a control signal 44' from the control unit 34. The one or more signals 46' from the signal generator 42 are fed to the summer 30 to be added to the processed signal 28' and being fed to the loudspeaker 6 for generation of one or more indicator signals.

In an embodiment, the one or more signals 46' from the signal generator 42 are fed to the processing unit 26, e.g. via the summation unit 20, to enable hearing loss compensation of the signal(s) 46' from the signal generator 42.

The one or more signals 46' may generate one or more beeps and/or a voice message. The signals 22', 24', 28', 44' may be single and/or multi-band signals.

Optionally, the signal processor unit 4 comprises a memory unit 48. The memory unit 48 is connected to the control unit 34. The hearing instrument 1 is configured to store at least one variable indicating user input from the user interface in the memory unit. Furthermore, the hearing instrument is configured for storing sets of variables including one or more operation parameters, e.g. state variables, filter coefficients, environment parameter, etc., in the memory unit.

The controller is configured to compare the first state and the second state in a compare function. Further, the control unit is configured to operate according to user feedback settings. The user feedback settings may be determined by the output of the compare function and/or by the content of a look-up table. The look-up table may be updated in an update state and/or during operation of the hearing instrument. A set of variables including subsequent user input via the user interface may be stored in the memory unit 48 according to the user feedback settings.

Figure 3:
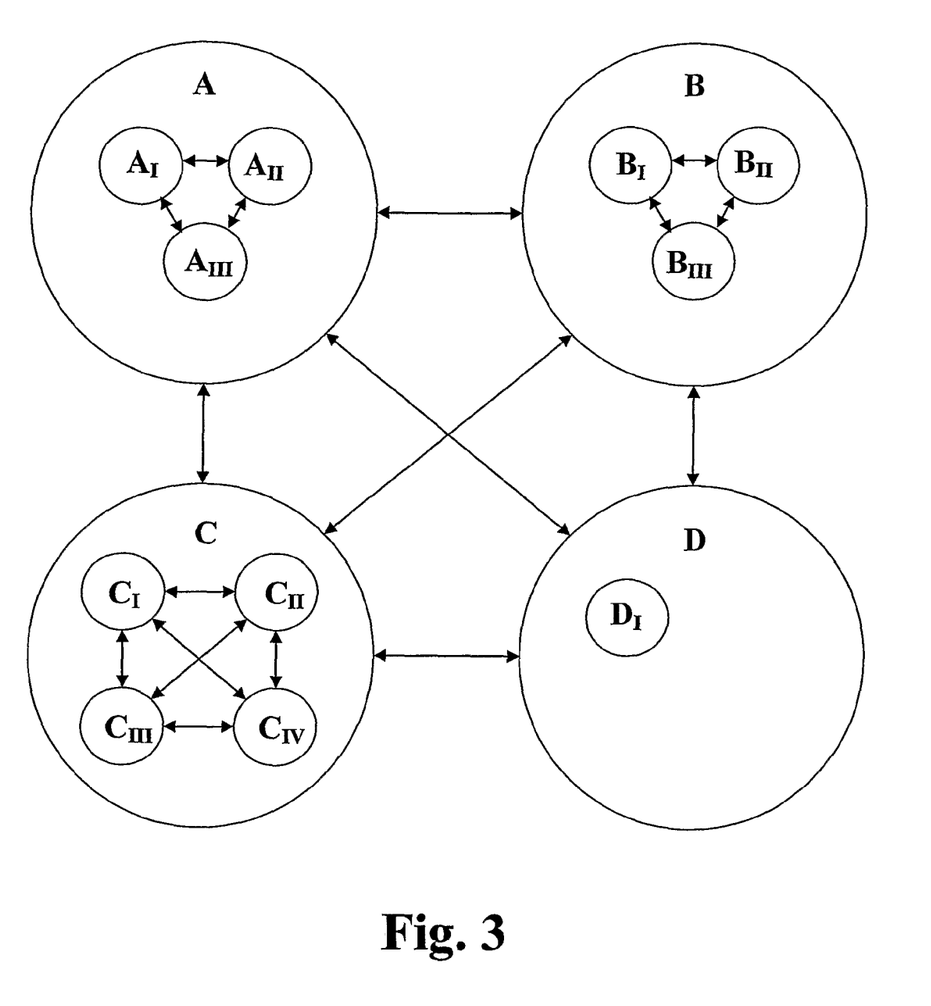
FIG. 3 schematically illustrates states of operation of a hearing instrument.

FIG. 3 schematically illustrates the operation of a hearing instrument. In the illustrated embodiment, the main state A comprises the sub states $A_I$, $A_{II}$, $A_{III}$, the main state B comprises the sub states $B_I$, $B_{II}$, $B_{III}$, the main state C comprises the sub states $C_I$, $C_{II}$, $C_{III}$, $C_{IV}$, and the main state D is an update state wherein the switching strategy hearing instrument is updated. The hearing instrument may be configured to switch to the update state D automatically or in response to an input from the user, e.g. in response to an input via the user interface. In an embodiment, the hearing instrument automatically switches to the update state prior to switching off the hearing instrument. The hearing instrument may be configured to automatically switch to the update state when the hearing is placed in a docking station, e.g. for recharging and/or update of the switching strategy via the docking station. Each main state comprises one or more sub states. Update of the switching strategy may be based on data stored in a memory unit of the hearing instrument.

One or more operating parameters of the hearing instrument may be set or adjusted according to the state of the hearing instrument. One or more operating parameters, the values of which change during operation of the hearing instrument, may define the state of the hearing aid.

FIGS. 4-7 are exemplary time lines showing operation according to different user feedback settings for an embodiment of a hearing instrument. The hearing instrument operates according to one or more sets of user feedback settings. According to a first set of user feedback settings, no indicator signals are emitted to indicate switching between the first state and the second state, and no input is allowed from the user. According to a second set of user feedback settings, no indicator signals are emitted to indicate different changes in the operation of the hearing instrument, and input is allowed from the user during a first input period after switching from the first state to the second state.

Figure 4:
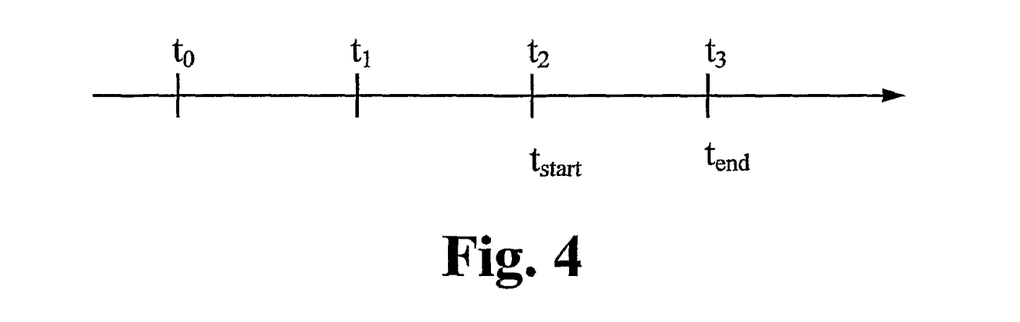
FIGS. 4-7 are exemplary time lines showing operation of a hearing instrument according to different sets of user feedback settings, FIG. 8 schematically illustrates an exemplary signal processor unit.

In FIGS. 4-7, the hearing instrument automatically switches from a first state to a second state at time to, i.e. one or more hearing aid parameters change at time $t_0$. The change of the one or more hearing aid parameters is monitored, e.g. by comparing the operating parameters in the compare function, and the controller operates according to the feedback settings. In case of a change requiring feedback, the hearing instrument is configured to emit indicator signals via the microphone. In FIG. 4, a first sound indicator signal at time $t_1$ is emitted indicating to the user that a state change has occurred, a second sound indicator signal indicating the beginning of a user input period is emitted at time $t_2$, and a third sound indicator signal indicating the end of a user input period is emitted at time $t_3$ according to the user feedback settings.

Figure 5:
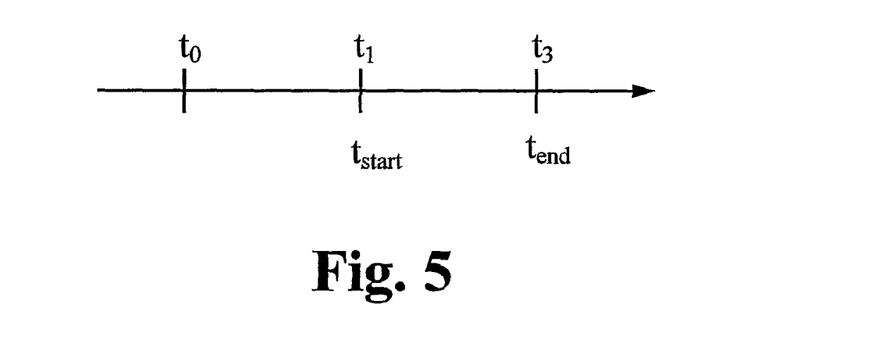
Figure 6:
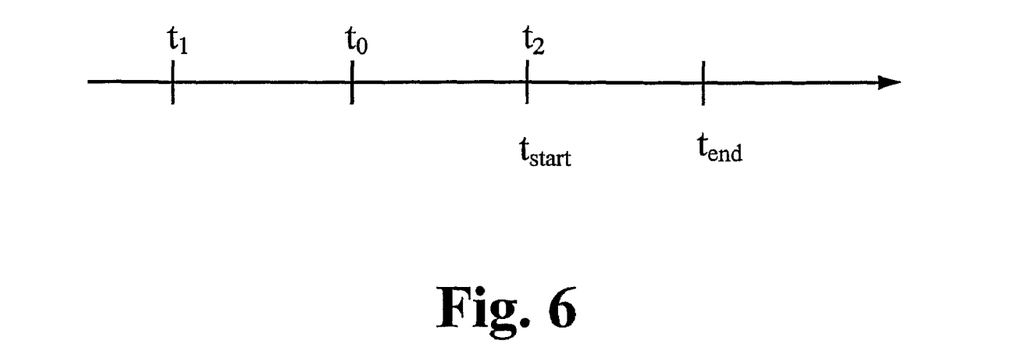

One or more indicator signals may be omitted according to the user feedback settings, e.g. as illustrated in FIG. 5, where emission of the second indicator signal at time $t_2$ is omitted and the first indicator signal emitted at time $t_1$ indicates change of state and beginning of input period, such as a time limited input period, wherein the hearing instrument is configured to receive user input/feedback. The first indicator signal may be emitted prior to switching from the first state to the second state as illustrated in FIG. 6.

The hearing instrument may be configured to receive input from the user continuously or during one or more input periods. A first input period start at time $t_{start}$ and end at $t_{end}$ as illustrated in FIGS. 4-7. Preferably, timing, duration and number of input periods are determined by the user feedback settings.

The first input period may begin and end at any suitable time, e.g. $t_{start}$ may be equal to one or more of $t_0$, $t_1$, $t_2$, and $t_{end}$ may be equal to $t_3$. In an embodiment, the end of the input period is set by either the end time according to the user feedback settings or the time where a state change requiring user feedback occurs whichever occurs first. The first input period may have any suitable length, e.g. from about 5 seconds to about 5 minutes, such as from about 15 seconds to about 1 minute, preferably around 30 seconds.

Figure 7:
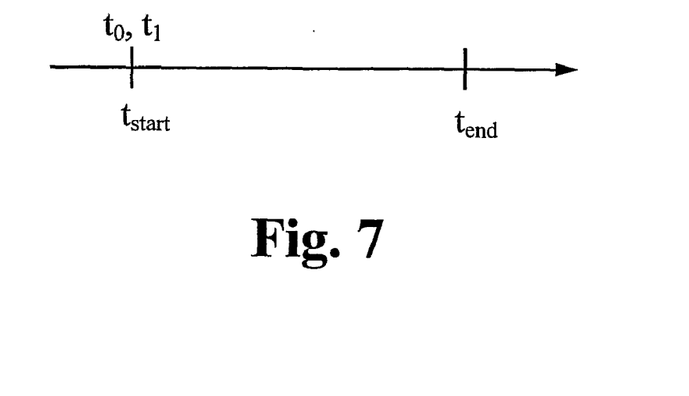

FIG. 7 is an exemplary time line showing operation of a hearing instrument according to a set of user feedback settings. In this embodiment $t_0$, $t_1$ and $t_{start}$ are substantially simultaneous and the length of the first input period ($t_{end} - t_{start}$) is 30 seconds.

Figure 8:
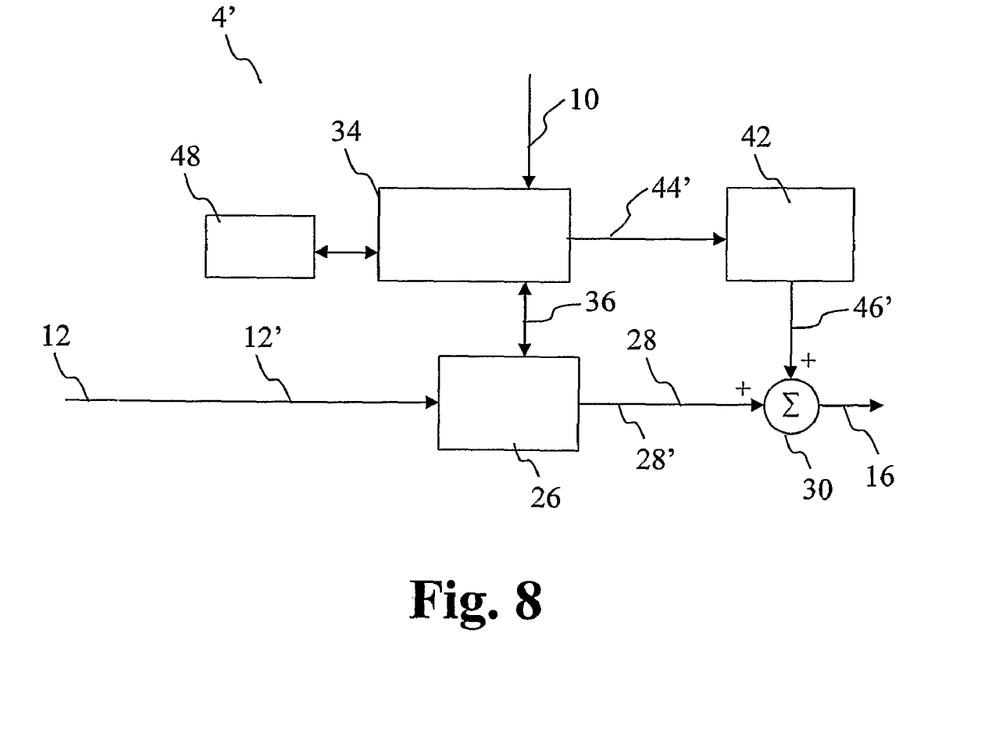

FIG. 8 schematically shows an exemplary signal processor unit 4' without feedback cancellation. The input signal 12' is fed to a processing unit 26 via connection 24. The processing unit 26 may comprise single or multi-band signal processing, and the processed signal 28' is fed to a summer 30. The output of the summer 30 is fed to the loudspeaker 6 via connection 16.

The signal processor unit 4' shown in FIG. 8 further comprises a control unit 34. The control unit 34 is connected to the processing unit 26 via connection 36. The control unit 34 may control and/or monitor one or more operating parameters of the signal processing in the processing unit 26 according to output from the user interface on connection 10.

The control unit 34 may monitor one or more operating parameters of the processing unit 26. The processing unit may adapt the signal processing, i.e. switch from a first state to a second state based on the input signal 12'. The signal processor unit 4' in FIG. 8 further comprises a signal generator 42. The signal generator 42 is configured to generate one or more signals in response to a control signal 44' from the control unit 34. The one or more signals 46' from the signal generator 42 are fed to the summer 30 to be added to the processed signal 28' and being fed to the loudspeaker 6 for generation of one or more indicator signals. The one or more signals 46' may generate one or more beeps and/or a voice message.

Optionally, the signal processor unit 4' comprises a memory unit 48. The memory unit 48 is connected to the controller 34. The hearing instrument is configured to store at least one variable indicating user input from the user interface in the memory unit. Furthermore, the hearing instrument is configured for storing sets of variables including one or more operation parameters, e.g. state variables, filter coefficients, environment parameter, etc., in the memory unit.

Figure 9:
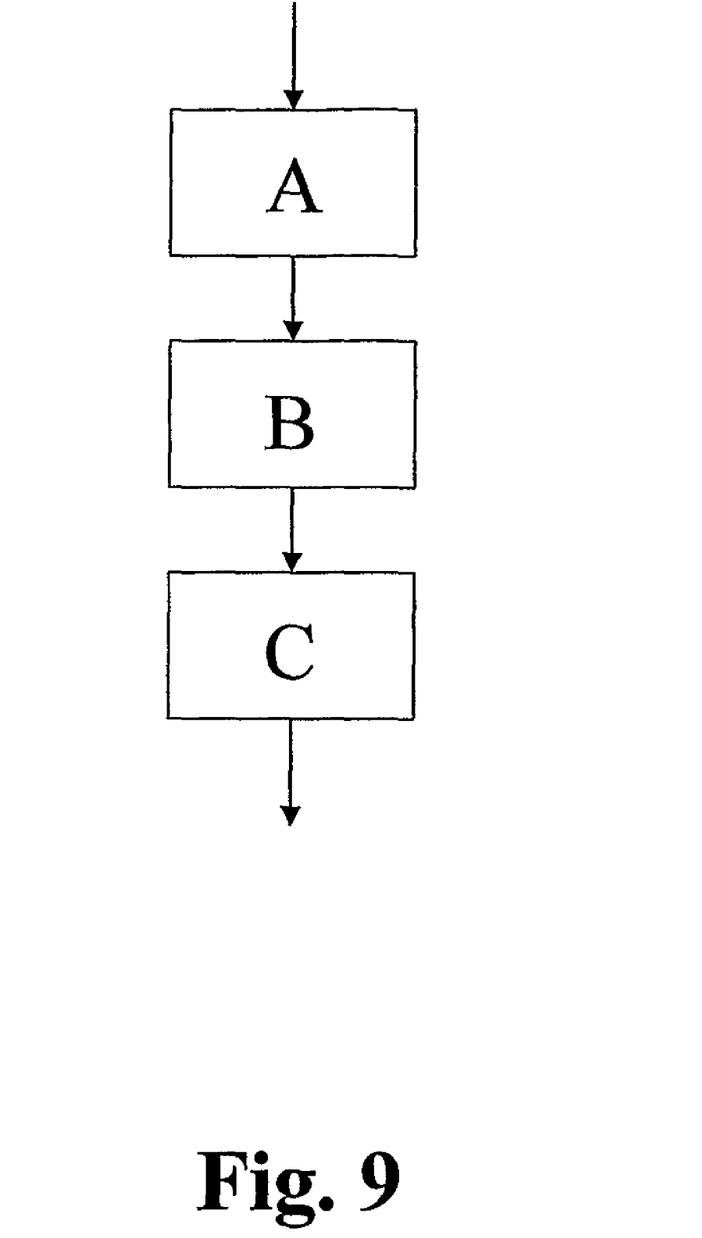
FIG. 9 is a flow diagram illustrating the method.

FIG. 9 is a flow diagram of an exemplary method of operating a hearing instrument operating according to one or more hearing aid parameters and having a user interface and being configured for automatic switching between a first state and a second state, according to some embodiments. The method comprises step A of monitoring one or more hearing aid parameters in order to identify a state change, step B of determining the user feedback settings if a state change has occurred, and step C of enabling user feedback via the user interface according to the user feedback settings. The method may further comprise the step of adjusting a set of user feedback settings based on the monitoring of the one or more hearing aid parameters. The method may further comprise the step of enabling user feedback in a predetermined period.

The invention claimed is:
1. A hearing instrument comprising:
a microphone for converting sound into an electric audio signal;
a signal processor unit coupled to the microphone, the signal processor unit configured for operating in a plurality of states that include at least a first state and a second state, wherein the signal processor unit is configured for automatically switching at least the first state and the second state according to a switching strategy;
a speaker coupled to the signal processor unit; and
a user interface for receiving a user feedback regarding an automatic switching between the first state and the second state, wherein the user interface is communicatively connected to the signal processor unit and is configured to provide at least one control signal to the signal processor unit in response to the user feedback;
wherein the signal processor unit is configured to receive the control signal in a predetermined input period upon the automatic switching between the first state and the second state.

2. The hearing instrument according to claim 1, wherein the automatic switching between the first state and the second state comprises an automatic switching from the first state to the second state, and wherein the signal processor unit is configured to receive the at least one control signal from the user interface in the predetermined input period upon the automatic switching from the first state to the second state.

3. The hearing instrument according to claim 2, wherein the user feedback comprises a negative feedback regarding the automatic switching, and the user interface is configured to provide the at least one control signal to the signal processor unit in response to the negative feedback.

4. The hearing instrument according to claim 3, wherein the signal processor unit is configured to switch from the second state back to the first state after receipt of the at least one control signal.

5. The hearing instrument according to claim 1, wherein the user feedback comprises a positive feedback regarding the automatic switching, and the user interface is configured to provide the at least one control signal to the signal processor unit in response to the positive feedback.

6. The hearing instrument according to claim 1, wherein the first state and the second state are main states having predefined hearing instrument parameters.

7. The hearing instrument according to claim 1, wherein the first state and the second state are sub states within a main state.

8. The hearing instrument according to claim 1, further comprising a signal generator for providing a first signal to indicate that an operation of the signal processor is being switched, has been switched, or will be switched, from the first state to the second state.

9. The hearing instrument according to claim 8, wherein the signal generator is configured to provide a second signal after the first signal is provided.

10. The hearing instrument according to claim 9, wherein the second signal is for indicating an end of an evaluation period, a beginning of a user-input period, or an end of the user-input period.

11. The hearing instrument according to claim 9, wherein the signal generator is further configured to provide a third signal after the second signal is provided.

12. The hearing instrument according to claim 11, wherein the third signal is for indicating an end of a user-input period or receipt of the feedback.

13. The hearing instrument according to claim 1, wherein the predetermined input period is a duration that is less than 30 seconds.

14. The hearing instrument according to claim 1, wherein the user interface is configured for allowing a user to selectively input a negative feedback or a positive feedback as the user feedback.

15. The hearing instrument according to claim 1, wherein the signal processor unit comprises a compare function that is configured to monitor operating parameters of the hearing instrument and provide an output as a result of the comparison.

16. The hearing instrument according to claim 15, wherein the signal processor unit is configured to determine a user feedback setting, and enable the user interface for receiving the user feedback according to the user feedback setting and the output of the compare function.

17. The hearing instrument according to claim 1, wherein the user interface is configured for automatic voice recognition and generation of the control signal in response to the automatic voice recognition.

18. The hearing instrument according to claim 1, wherein the user interface comprises a switch or a push-button.

19. The hearing instrument according to claim 1, wherein the user interface comprises a remote control.

20. The hearing instrument according to claim 1, further comprising a memory unit for storing information that is associated with the user feedback.

21. The hearing instrument according to claim 20, wherein the information comprises one or more of a state variable, a filter coefficient, and an environment parameter.

22. The hearing instrument according to claim 20, wherein the signal processor unit is configured to update the switching strategy based at least in part on the information stored in the memory unit.

23. The hearing instrument according to claim 22, wherein the signal processor unit is configured to continuously update the switching strategy.

24. The hearing instrument according to claim 22, wherein the plurality of states includes an update state for updating the switching strategy.

25. The hearing instrument according to claim 1, wherein the plurality of states include a third state, and wherein the signal processor unit is configured for switching to a third state in response to another control signal from the user interface.

26. The hearing instrument according to claim 1, wherein the signal processor unit is configured to receive the control signal by allowing the user interface to receive the user feedback.

27. A method of operating a hearing instrument that operates according to one or more hearing aid parameters, the hearing instrument having a user interface and being configured for automatic switching between a first state and a second state, the method comprising:
monitoring the one or more hearing aid parameters to identify a state change;
determining a user feedback setting; and
when the state change is identified, enabling user feedback via the user interface according to the user feedback setting.

28. The method according to claim 27, wherein the act of enabling user feedback comprises enabling the user feedback in a predetermined period.

29. The method according to claim 27, wherein the user feedback setting includes information selected from the group consisting of an input period length, a type of indicator signal, and an indicator signal scheme.

* * * * *